United States Patent [19]
Akutagawa et al.

[11] Patent Number: 5,485,744
[45] Date of Patent: Jan. 23, 1996

[54] SULFURIC ACID CONCENTRATION SENSOR FOR LEAD STORAGE BATTERY

[75] Inventors: Tadamasa Akutagawa, 19-8, Kamiikedai 1-chome, Ota-ku, Tokyo 145; Shigeru Sano, Takatsuki, both of Japan

[73] Assignees: Tadamasa Akutagawa, Tokyo; Yuasa Corporation, Osaka, both of Japan

[21] Appl. No.: 204,418

[22] PCT Filed: Sep. 16, 1992

[86] PCT No.: PCT/JP92/01178

§ 371 Date: Mar. 15, 1994

§ 102(e) Date: Mar. 15, 1994

[87] PCT Pub. No.: WO93/06452

PCT Pub. Date: Apr. 1, 1993

[30] Foreign Application Priority Data

Sep. 18, 1991 [JP] Japan .................... 3-237794

[51] Int. Cl.$^6$ .................................. G01N 9/00
[52] U.S. Cl. ............................ 73/61.49; 429/90
[58] Field of Search ............... 73/54.41, 61.49, 73/64.53, 32 A; 429/90

[56] References Cited

U.S. PATENT DOCUMENTS

| | | | |
|---|---|---|---|
| 2,711,646 | 6/1955 | Mendousse | 73/64.53 |
| 3,661,652 | 5/1972 | Uitenbroek | 429/90 |
| 4,308,817 | 1/1982 | Peterson | 429/90 |
| 4,721,874 | 1/1988 | Emmert | 73/54.41 |
| 4,783,987 | 11/1988 | Hager et al. | 73/54.41 |
| 4,788,466 | 11/1988 | Paul et al. | 73/54.41 |
| 4,961,345 | 10/1990 | Tsuruoka | 73/32 A |

FOREIGN PATENT DOCUMENTS

| | | | |
|---|---|---|---|
| 0134480 | 10/1981 | Japan | 429/90 |
| 59-46837 | 3/1984 | Japan . | |
| 60-188395 | 12/1985 | Japan . | |
| 40016743 | 1/1992 | Japan | 73/61.49 |

*Primary Examiner*—Hezron E. Williams
*Assistant Examiner*—Michael J. Brock
*Attorney, Agent, or Firm*—Evenson, McKeown, Edwards & Lenahan

[57] ABSTRACT

A sulfuric acid concentration sensor for a lead storage battery comprising a quartz resonator changing its characteristic frequency in a manner of single-valued function according to the change of sulfuric acid concentration and an oscillation circuit (20) oscillating the quartz resonator, the quartz resonator is immersed in an electrolyte (6) so as to be oscillated, and a characteristic frequency of the quartz resonator at this moment is obtained so as to determine the sulfuric acid concentration. The sensor of this invention is compact in its size, simple in its structure and cheap in its cost, so that it can be applied to a lead storage battery for automobile.

10 Claims, 9 Drawing Sheets

SULFURIC ACID CONCENTRATION SENSOR FOR LEAD STORAGE BATTERY

TECHNICAL FIELD

This invention relates to a sensor for detecting a sulfuric acid concentration of an electrolyte for a lead storage battery.

BACKGROUND ART

The greater part of a lead storage battery is used for starting an automobile. When a charging condition of the lead storage battery is not sufficient, the battery is short of its residual capacity so that the automobile becomes unable to be started. If the charging condition is known previously, countermeasures such as execution of supplementary charging etc. may be taken before stopping the automobile. However, it has been impossible to know the charging condition in advance, such that much inconvenience has been experienced. Charging of the lead storage battery has been done by supplying electric power from a generator, and a supply voltage has been controlled by a regulator to a constant value so as to avoid an overcharging. However, the voltage of the lead storage battery changes delicately depending on a discharge quantity, a temperature, a frequency of charge and discharge, and the history of the battery etc. For this reason, the overcharging of the battery can not be avoided by only a control of the voltage through means of the regulator i.e. only a control of voltage determined on the electric circuit side. This has been a major cause of the short service life of the lead storage battery for an automobile.

From the reasons as mentioned above, it has been strongly demanded to detect a charging condition or discharging condition of the lead storage battery.

As a method for detecting the charge and discharge conditions of lead storage battery, systems utilizing the following four methods for measuring a concentration of sulfuric acid forming an electrolyte have been known. However, any system has been expensive and not practical for use in the lead storage battery for automobile.

(1) Refractive index measuring method

A system of this method is composed of a light emitting diode, a light receiving diode and an optical path. This is a method for measuring a sulfuric acid concentration by making use of a property of sulfuric acid forming the electrolyte to change its refractive index according to its concentration. This method has already been put in practical use for a stationary lead storage battery. However, it has been impossible to minimize a size and reduce a cost because of necessity for executing a photoelectric conversion and preventing the optical path from being contaminated. For this reason, this method is not used for the lead storage battery for automobile.

(2) Specific gravity measuring method

This is a method for measuring a specific gravity of sulfuric acid by using a float. This is an inexpensive and easy method. In addition, this is a very useful and certain method in a manual operation such as maintenance. However, this method includes difficulties in respect of cost and structure in order to transmit measured data as electric signals to a data processor located at a center of automobile.

(3) Electrochemical method

This is a method in which an electrode system for sensor comprising components of metal, sulfuric acid and metal oxide is separately installed, and the concentration is measured utilizing such a property that an electromotive force depends on the sulfuric acid concentration. However, an appropriate electrode for this purpose can not be obtained yet. Only one put in practical use is an electrode system comprising components of lead, sulfuric acid and lead dioxide. However, this system is not appropriate for practical use because periodic reproduction of both electrodes is required.

(4) Electric conductivity method

This is a method for measuring an electric conductivity of sulfuric acid. However, since the electric conductivity of sulfuric acid concentration becomes a maximum in a condition where about a quarter of the sulfuric acid is discharged, the sulfuric acid concentration can not be determined from the electric conductivity unequivocally. In addition, it is required to process data in consideration of various factors such as stirred condition of electrolyte and temporary fluctuation due to external electric noise etc., so that this method is very complicated, expensive and lacks in reliability.

Further, the sulfuric acid forming the electrolyte of lead storage battery is strongly acidic, and an inside of battery is under a very strong oxidation-reduction atmosphere. For this reason, there are very many limitations in materials This invention is made in consideration of the above-mentioned problems, and an object of this invention is to provide a sulfuric acid concentration sensor appropriate to a lead storage battery for an automobile which is small in its size, simple in its structure and cheap in its price.

DISCLOSURE OF THE INVENTION

This invention provides a sulfuric acid concentration sensor for a lead storage battery comprising a quartz resonator changing its characteristic frequency in a manner of single-valued function according to a change of sulfuric acid concentration and an oscillation circuit oscillating the quartz resonator, the quartz resonator being immersed in an electrolyte so as to be oscillated, and a characteristic frequency of the quartz resonator at this moment being obtained so as to determine the sulfuric acid concentration.

When the quartz resonator is oscillated by the oscillation circuit, the characteristic frequency of the quartz resonator is changed by a reaction from the electrolyte. Since this change is in a single-valued functional relation with a change of a sulfuric acid concentration of the electrolyte, the sulfuric acid concentration can be determined by obtaining the characteristic frequency.

BRIEF DESCRIPTION OF THE DRAWINGS

10 is an enlarged partial view viewed in a direction of arrow X of FIG. 8.

BEST MODE FOR CARRYING OUT THE INVENTION (Embodiment 1)

Figure 1:
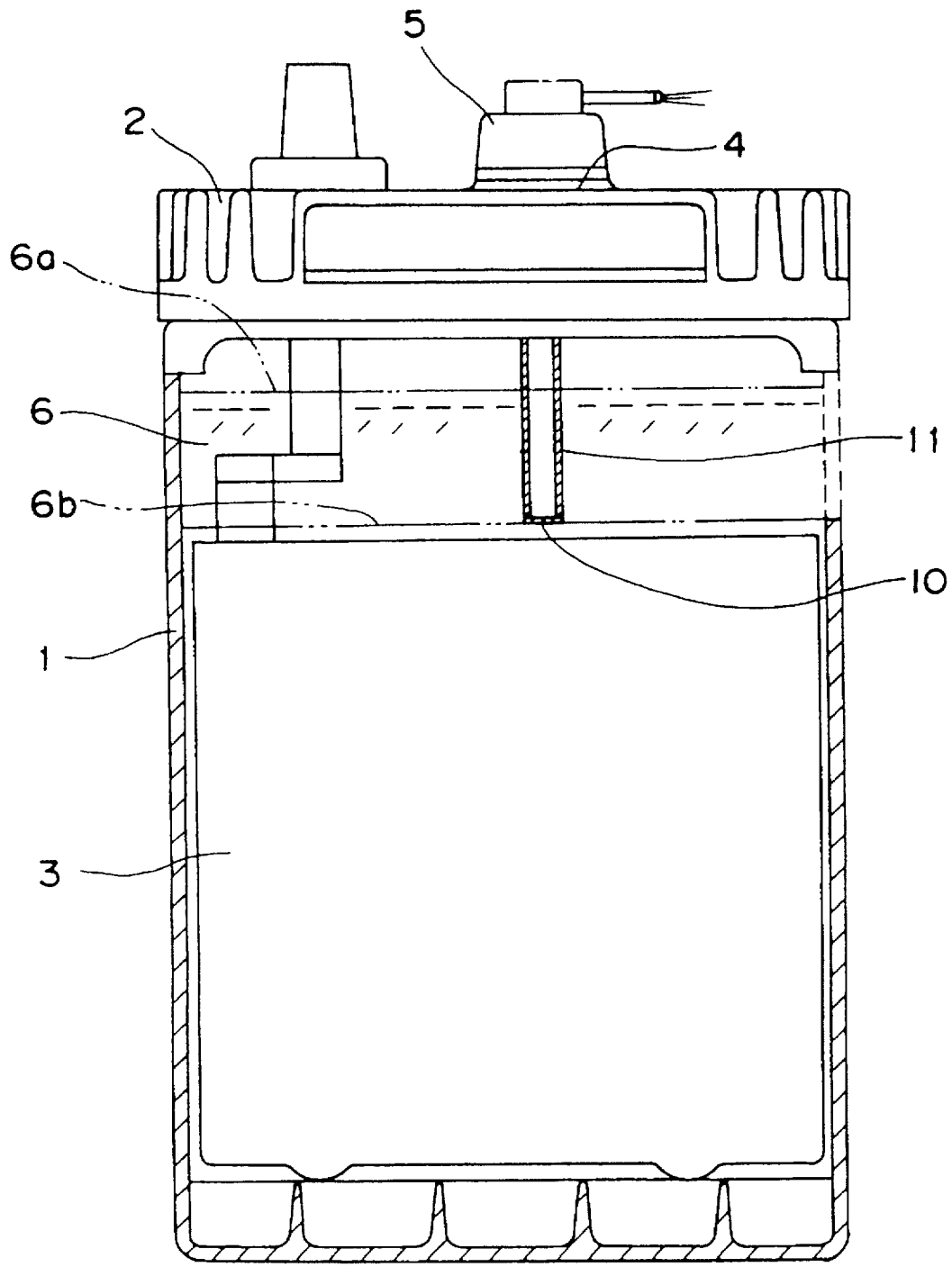
FIG. 1 is a partially sectional vertical view showing a lead storage battery for automobile adopting a sulfuric acid concentration sensor of embodiment 1.

FIG. 1 is a partially sectional vertical view showing a lead storage battery for an automobile adopting a sulfuric acid concentration sensor of this embodiment. In this figure, 1 denotes a container body, and 2 denotes a cover. A plate 3, along with other plates, are housed in the container body 1 in a state of immersion in a sulfuric acid 6 forming an electrolyte. Reference 6a indicates a liquid surface of the sulfuric acid 6, and 6b is a lower limit line of the liquid surface of the sulfuric acid 6. A filling port 4 is formed on the cover 2, and a pore plug 5 is inserted in the filling port 4 so as to plug it. A sulfuric acid concentration sensor of this embodiment is installed in the port plug 5. This lead storage battery offers a voltage of 12 V and a capacity of 35 Ah, and is divided into six chambers with respective voltages of 2 V each. The sulfuric acid concentration sensor is installed in each chamber.

Figure 2:
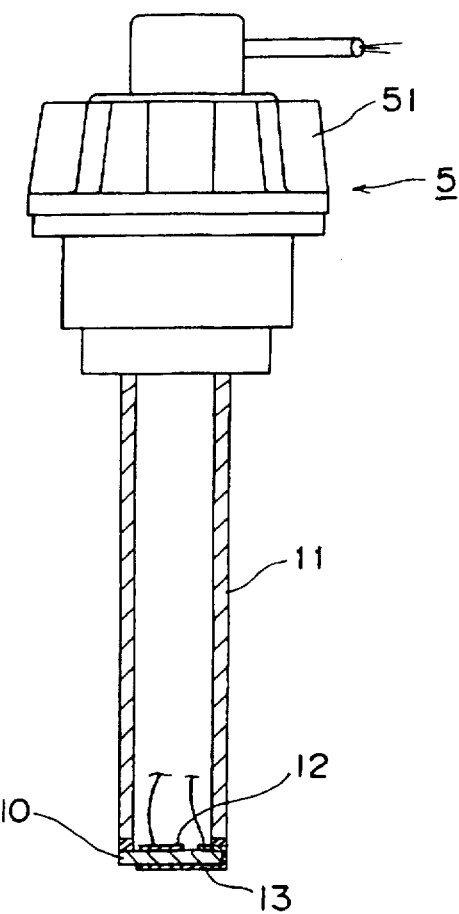
FIG. 2 is an enlarged partially sectional vertical view of a port plug of embodiment 1.
Figure 3:
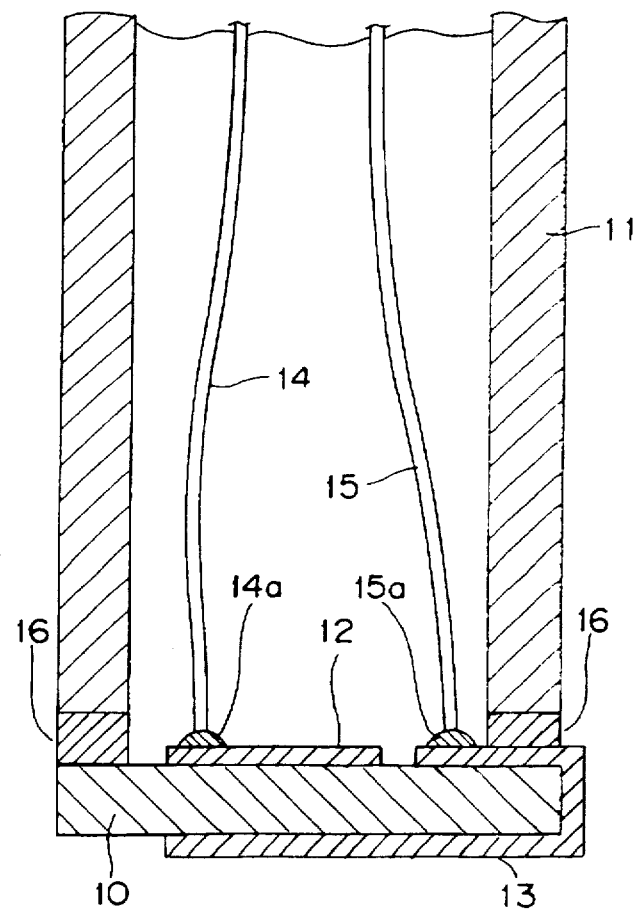
FIG. 3 is a partially enlarged view of FIG. 2.

FIG. 2 is an enlarged partially sectional vertical view of the born plug 5. The sulfuric acid concentration sensor of this embodiment is equipped with a quartz resonator plate 10, an oscillation circuit 20 and an interface circuit 30. The quartz resonator plate 10 is generally a disc smaller than or equal to 10 mm. The oscillation circuit 20 and the interface circuit 30 are assembled in one integrated circuit so as to be incorporated in a cover portion 51 of the port plug 5. Reference 11 denotes a holder tube extending perpendicularly from the cover portion 51, and the quartz resonator plate 10 is installed in a horizontal position so as to plug a bottom opening of the holder tube 11. The quartz resonator plate 10 is stuck to the holder tube 11 by means of an adhesive agent such as an ultraviolet setting resin for example, and the holder tube 11 is thereby sealed to be protected from the sulfuric acid 6 which will enter its inside. The length of the holder tube 11 is preset such that the quartz resonator plate 10 is positioned at the lower limit line of the liquid surface of the electrolyte. As shown by FIG. 3 which is an enlarged partial view of FIG. 2, electrodes 12 and 13, composed of conductive films, are attached to both surfaces of the quartz resonator plate 10 so as to form the quartz resonator operating as an electro-mechanical resonator having a natural oscillating mode. The electrode 12 is attached to an inside surface (upper surface) of the quartz resonator plate 10, and the electrode 13 is attached from an outside surface (lower surface) through to the inside surface. The ends of the lead wires 14 and 15 are stuck to the electrodes 12 and 13 by means of conductive adhesive agents 14a and 15a. Other ends of the lead wires 14 and 15 are connected to the oscillation circuit 20. The quartz resonator plate 10 contacts the sulfuric acid 6 at its electrode 13 side surface only. The cover portion 51 is the same as that of a conventional port plug, so that the sulfuric acid concentration sensor of this embodiment is installed utilizing the conventional port plug as it is.

A crystal forming the quartz resonator plate 10 comprises a single crystal of silicon dioxide having a piezo-electric property. Crystal plates cut out at various angles relative to a crystal axis form the above-mentioned quartz resonator except for a crystal plate having a plane perpendicular to the Z-axis. For example, a crystal plate having a plane perpendicular to the X-axis produces a longitudinal vibration in a direction of the plate thickness, and a crystal plate having a plane perpendicular to Y-axis or an intermediate direction between the Y-axis and the Z-axis produces a shear vibration in the direction of the plate thickness. Among the crystal plates producing the shear vibration, those having a plane perpendicular to the Y-axis are called a Y-cut, and those having a plane in an intermediate direction between the Y-axis and the Z-axis and perpendicular to a direction of 55°45" inclined from the Z-axis are called an AT-cut. It is known that the characteristic frequency of the quartz resonator plate exhibits respective characteristic temperature coefficients depending upon the cut angle. As a method for indicating the cut angle of the quartz resonator plate, there is a method of indication by arranging a thickness axis, a length axis, a rotation axis (length axis l or width w) and a rotation angle, in this order. According to this method, a Y-cut is indicated as (yxl) 0° and an AT-cut is indicated as (yxl) 35°15". A resonator plate having an optimum temperature coefficient, i.e. a temperature coefficient which compensates for a change in a specific gravity and a viscosity of sulfuric acid as described later, is selected from among those producing the shear vibration and is then used for the quartz resonator plate 10 of this embodiment. Further, a thickness of the quartz resonator plate 10 is determined by conversely obtaining it from a desired frequency because a characteristic frequency is related to a thickness of the plate.

The holder tube 11 is made of an insulating material provided with a resistance against the sulfuric acid, such as glass, ceramics and plastic etc. and having a coefficient of linear expansion as close to that of the quartz resonator plate 10 as possible. This is because of a consideration that the coefficient of linear expansion has an influence upon the characteristic frequency of the quartz resonator plate 10 through the deformation.

The electrode 13 is made of a material such as gold or tin oxide which does not change its property even when it contacts the sulfuric acid. In order to carry out a fine adjustment of the characteristic frequency, it is preferable to additionally deposit a proper amount of silver etc. onto the electrode 12 at a side not contacting the electrolyte.

Figure 4:
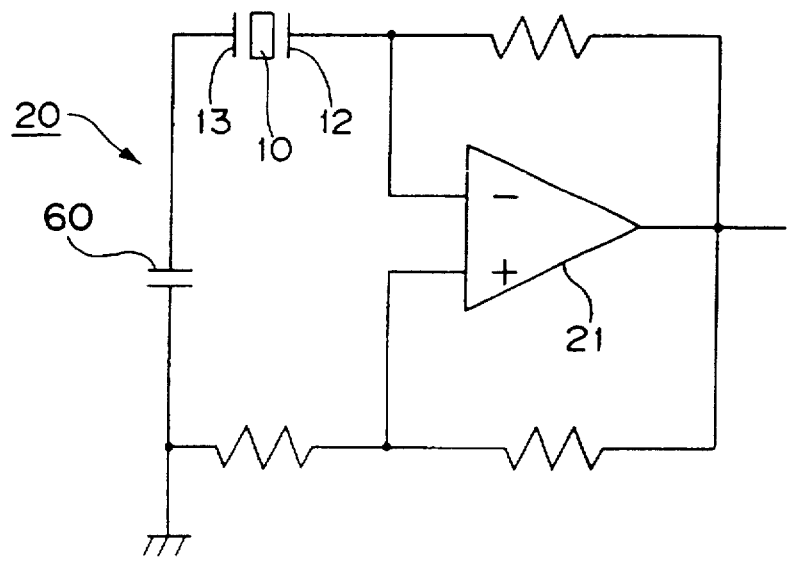
FIG. 4 is a circuit diagram showing an oscillation circuit of embodiment 1.

FIG. 4 is a circuit diagram showing the oscillation circuit 20. Reference 21 denotes an operational amplifier. In this circuit 20, the electrode 13 is in a grounded condition through a large capacity condenser 60 in respect of alternating current. For this reason, the oscillation circuit 20 has a characteristic that it can be oscillated and operated even if the electrode 13 is changed to be put under a voluntary direct current potential. This brings about such merits that a power of the oscillation circuit 20 can be supplied directly from the lead storage battery which is an object of measurement, and the sulfuric acid concentration sensor of this embodiment can be applied to any one of several serial chambers of the lead storage batteries which are serially-connected, i.e. have direct current potentials different from each other.

Figure 5:
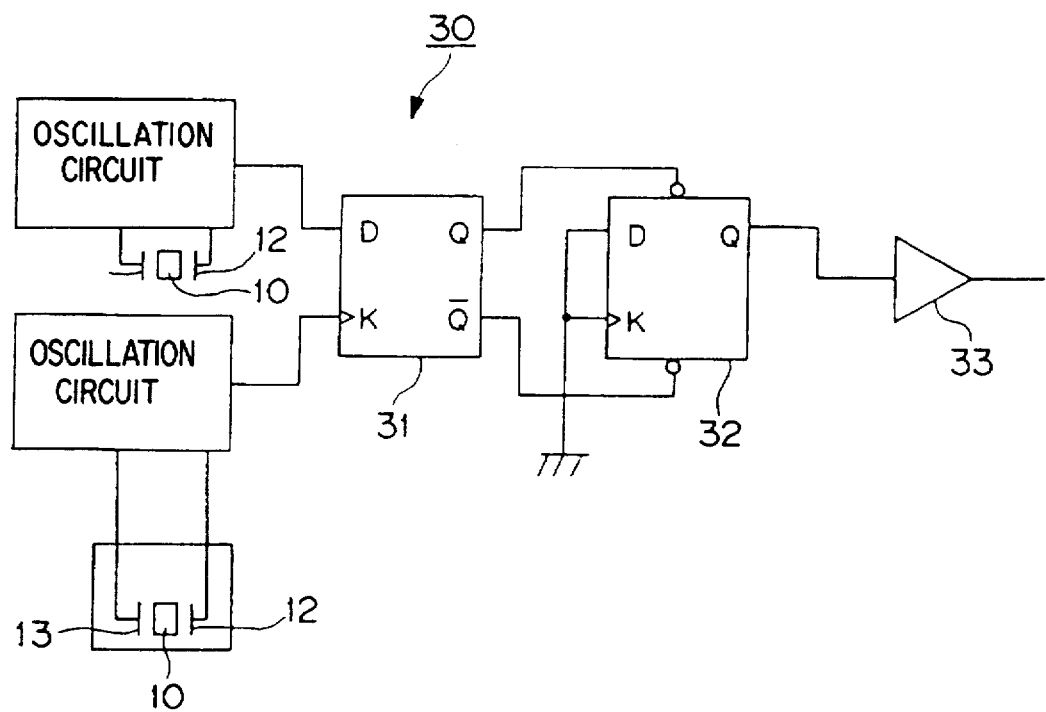
FIG. 5 is a circuit diagram showing an interface circuit of embodiment 1.

The interface circuit divides, or adds and subtracts, a frequency obtained by the oscillation circuit as mentioned above, or converts a frequency to voltage or converts a frequency to current; so as to ease a transmission to a distant place, improve a temperature coefficient of the measured value, or make the frequency conform to that of the receiving system at a place to which the frequency is transmitted. The interface circuit has a composition of circuit components as shown by FIG. 5. Namely, the interface circuit 30 is designed to compensate the temperature coefficient of the characteristic frequency of the quartz resonator, and at the same time, to extract only the amount of change in concentration of the electrolyte and to minimize a value itself of the frequency, by passing output frequencies of the two different oscillation circuits 20 through a frequency subtracting circuit comprising data latches 31 and 32. An output of the data latch 32 is fed to a line driver 33 in order to increase the noise-resistance during transmission.

The function of the interface will be described hereunder. When the quartz resonator comprising the quartz resonator plate 10 and the electrodes 12 and 13 is made to oscillate by the oscillation circuit 20 under a state of immersion in the sulfuric acid 6, the quartz resonator excites transverse waves in the sulfuric acid 6 through means of its viscosity, and the sulfuric acid 6 becomes a load of the quartz resonator as its reaction so that the characteristic frequency of the quartz resonator is lowered. It has been proved that the amount of decrease in the frequency is theoretically in proportion to a square root of a product of a specific gravity and a coefficient of viscosity of the sulfuric acid 6. In this instance, the amount of decrease in the frequency is influenced by changes of a specific gravity and a viscosity of the sulfuric acid 6 caused by the temperature change. The amount of decrease is about $-3$ ppm/°C. when the sulfuric acid concentration is 10%, and about $-5$ ppm/°C. when it is 39%, within a temperature range from 0° C. to 50° C., so that a temperature rise results in an increase of the frequency. In this embodiment, in order to positively allow the quartz resonator plate 10 i.e. the quartz resonator itself, to have a temperature coefficient compensating the influence caused by the foregoing temperature change, a quartz resonator plate which includes a cut angle θ ranging from 35°40" to 36°10" indicated by (yxl) θ, is used as occasion demands. This is by utilizing the fact that the characteristic frequency decreases at a rate of $-5.15$ ppm/°C. per 1° increase of cut angle in the vicinity of AT-cut. Thereby, an error caused by the temperature change in the measurement of the sulfuric acid concentration is reduced.

As for other temperature compensation methods, such methods can be considered as (1) methods of using a temperature compensation type condenser as the condenser 14, and (2) methods of using a temperature sensor such as a thermistor and compensating by a separately installed micro-computer on the basis of its signal.

Figure 6:
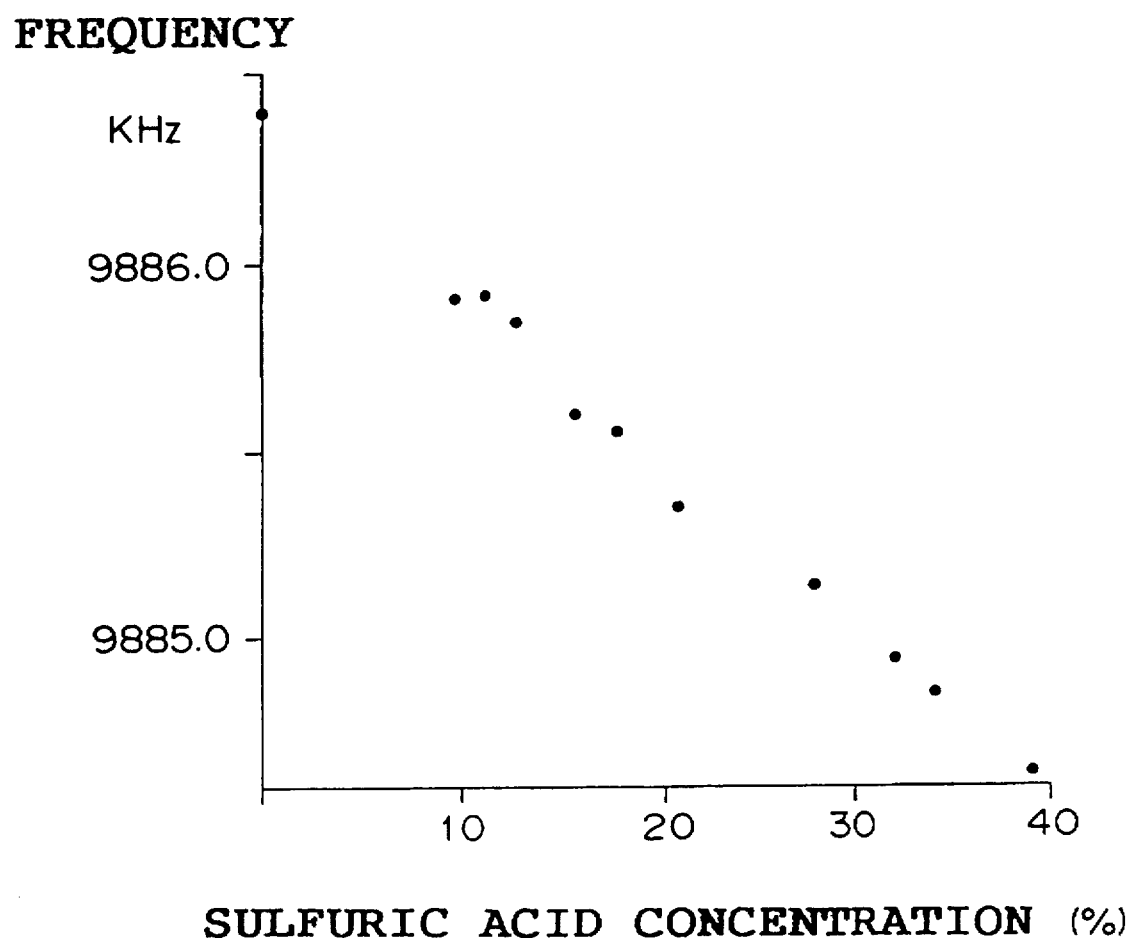
FIG. 6 is a diagram showing results obtained by measuring plural electrolytes having different sulfuric acid concentrations by using the sulfuric acid concentration sensor of embodiment 1.

FIG. 6 is a diagram showing the results obtained by measuring plural electrolytes having different sulfuric acid concentrations by using the sulfuric acid concentration sensor thus constructed. As is obvious from this diagram, the frequency of the quartz resonator is approximately in linear relationship to the sulfuric acid concentration. Therefore, when the frequency of the quartz resonator is obtained, the sulfuric acid concentration can be determined.

In the sulfuric acid concentration sensor thus constructed, the electrode 13 at the side contacting the sulfuric acid 6 of the quartz resonator plate 10 is grounded with respect to the alternating current, so that it can operate at any direct current potential. Therefore, the oscillation circuit 20 is able to oscillate normally, so that it is able to measure the sulfuric acid concentration of electrolyte in any one of several serial chambers of the lead storage battery, each of which is at different potentials.

Since the holder tube 11 is made of a material having a coefficient of linear expansion as close to that of the quartz resonator plate 10 as possible. there is no chance for the coefficient of linear expansion to influence the characteristic frequency of the quartz resonator plate 10 through the deformation. From this point again, the sulfuric acid concentration can be measured correctly.

Further, the quartz resonator plate 10 is positioned at the liquid surface lower limit line 6b of the electrolyte. Therefore, when a quantity of the electrolyte decreases to a level lower than the lower limit line 6b, the quartz resonator plate 10 will be exposed up above the liquid surface, and the oscillation frequency becomes abnormally high so that the measured value becomes abnormal. Consequently, this sensor also functions as a level gauge by detecting the abnormal value.

Moreover, the oscillation circuit 20 and the interface circuit 30 are incorporated in the cover portion 51 and are thereby located at positions very near to a place where the measurement is done, so that any electric noise influences arising within these spaces is very small. In addition, since the measured values are transmitted by the interface circuit 30 in the form of a signal resistant to the electric noise, an influence of electric noise arising between the place and the data processor located at the center of the automobile is also small.

Embodiment 2

Figure 7:
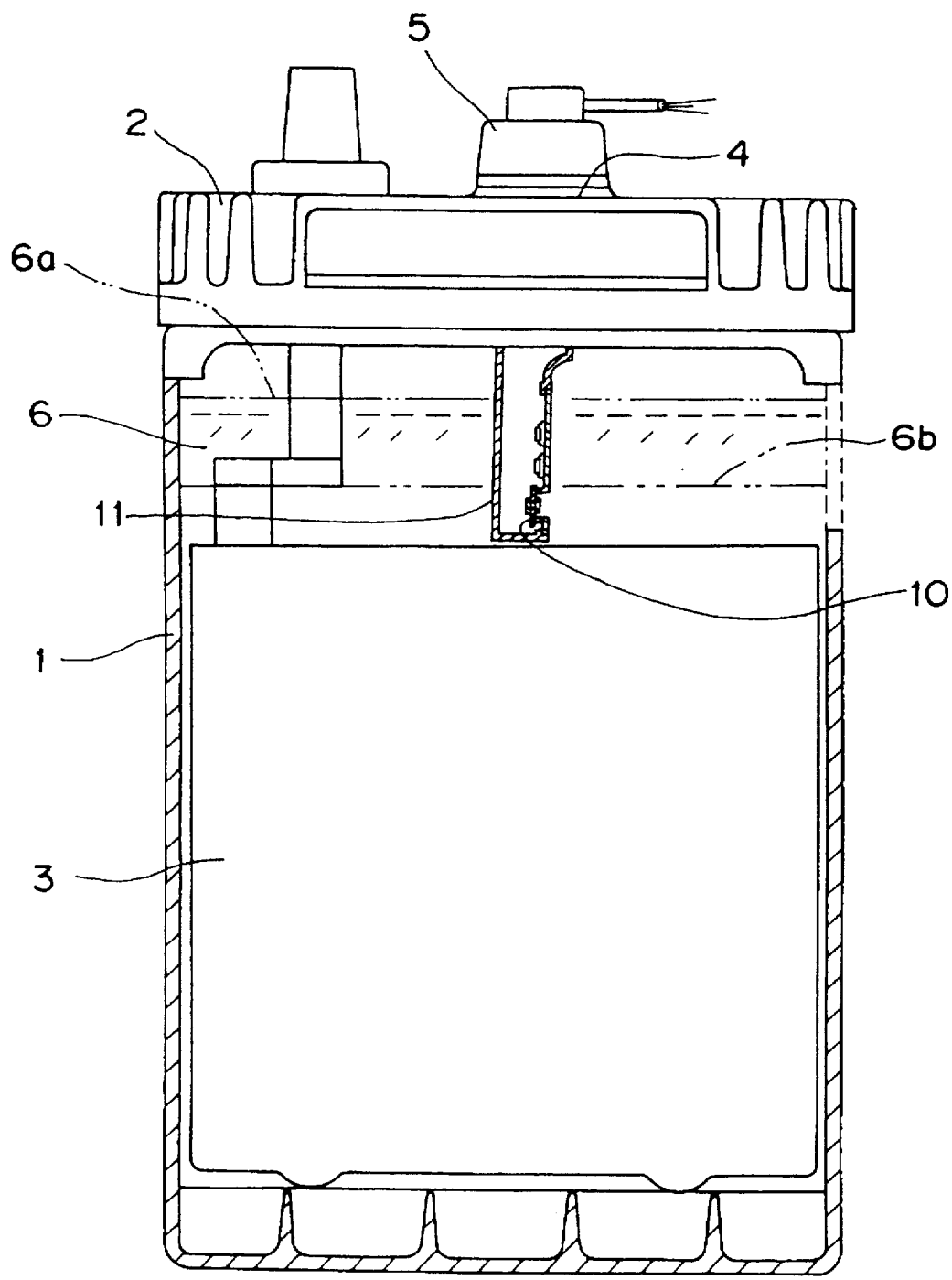
FIG. 7 is a partially sectional vertical view showing a lead storage battery for automobile adopting a sulfuric acid concentration sensor of embodiment 2.

FIG. 7 is a partially sectional vertical view showing a lead storage battery for an automobile adopting a sulfuric acid concentration sensor of this embodiment. The lead storage battery is the same as that of the first embodiment. In FIG. 7, the same components with those of FIG. 1 are attached with the same symbols.

Figure 8:
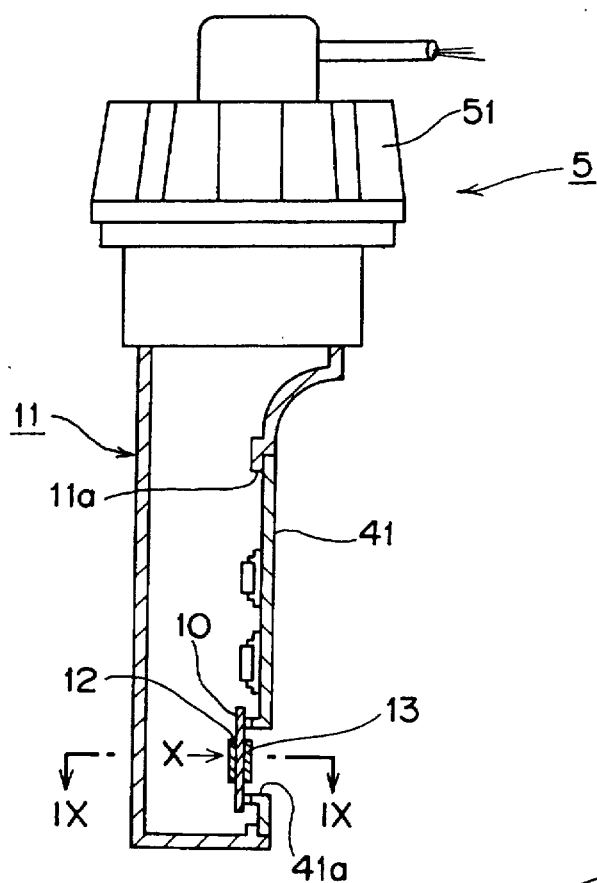
FIG. 8 is an enlarged partially sectional vertical view of a port plug of embodiment 2.
Figure 9:
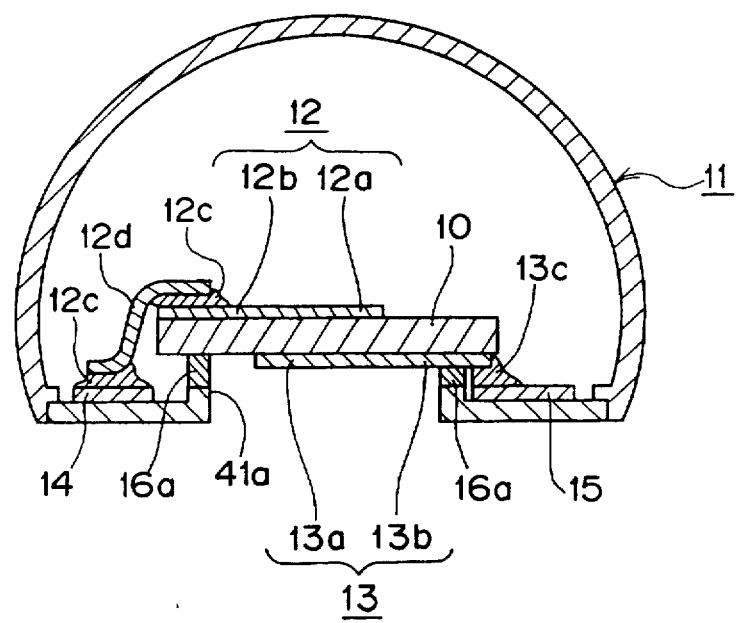
FIG. 9 is a sectional view taken on a line IX—IX of FIG. 8. FIG.
Figure 10:
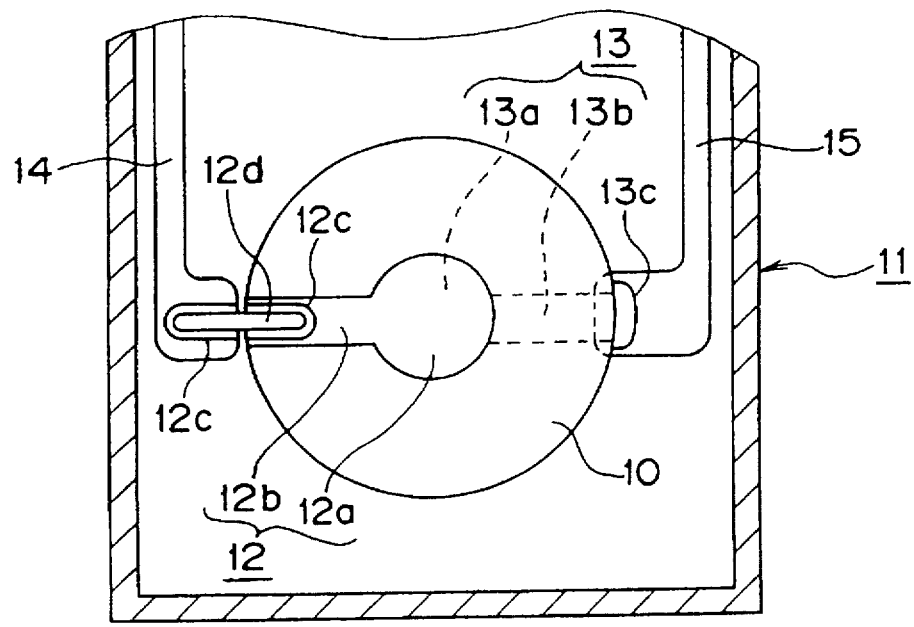

FIG. 8 is an enlarged partially sectional vertical view of a port plug 5, FIG. 9 is an enlarged sectional view taken on a line IX—IX of FIG. 8, and FIG. 10 is an enlarged partial view viewed in a direction of arrow X of FIG. 8. In these figures, the same components as those of FIG. 2 and FIG. 3 are attached with the same symbols. The sulfuric acid concentration sensor of this embodiment is also equipped with the quartz resonator plate 10, the oscillation circuit 20 and the interface circuit 30, and is installed utilizing the conventional port plug as it is.

The holder tube 11 has an opening 11a at its side surface, and a circuit substrate 41 is fitted in the opening 11a. The oscillation circuit 20 and the interface circuit 30 are assembled in one integrated circuit and equipped in the circuit substrate 41, and the quartz resonator comprising the quartz resonator plate 10 and the electrodes 12 and 13 attached to both surfaces thereof is also installed in the substrate. Both circuits 20 and 30 are installed on an inside of the circuit substrate 41 i.e. an inside of the holder tube 11, and the quartz resonator plate 10 is so installed as to close a circular opening 41a of the circuit substrate 41 from its inside. The quartz resonator plate 10 is secured to the opening 41a from its inside through means of an adhesive agent 16a such as an ultraviolet curing resin for example, so that it seals the opening 41a to prevent the sulfuric acid 6 from entering the opening. The opening 11a of the holder tube 11 is closed by the circuit substrate 41 provided with the quartz resonator plate 10 and sealed to prevent the sulfuric acid 6 from entering the opening. The quartz resonator plate 10 is installed at such a position that its upper end aligns with the liquid surface lower limit line 6b of the sulfuric acid 6.

The quartz resonator plate 10 only contacts the sulfuric acid 6 at its electrode 13 side surface. The reason is as follows. If the electrodes 12 and 13 located at both side surfaces are immersed in the electrolyte simultaneously, the oscillation circuit 20 becomes hard to operate so that conditions required for the oscillation circuit 20 will become severe because a large admittance of electrolyte is added to an inherent admittance of the quartz resonator plate 10.

A plating layer (not shown) of lead dioxide is formed on the electrode 13 side surface of the quartz resonator plate 10 so as to cover the electrode 13 as well. This plating layer is formed in such a way, for example, that the quartz resonator plate 10 on which the electrode 13 is formed is subjected to electroplating with the quartz resonator plate 10 immersed in lead nitrate solution and the obtained plating layer of metallic lead is anodically oxidized in sulfuric acid solution. A method such as a vacuum evaporation, a chemical vapor phase deposition or a chemical plating may be used in place of the electroplating. The electrode 12 installed on the inside surface side of the quartz resonator plate 10 is composed of a circular portion 12a located at a center of the quartz resonator plate 10 and a lead portion 12b extending from the circular portion 12a. The lead portion 12b is connected to a lead wire 14 through a conductive adhesive agent 12c, a conductive wire 12d and the conductive adhesive agent 12c. The electrode 13 installed on the outside surface side of the quartz resonator plate 10 is also composed of a circular portion 13a and a lead portion 13b, and is connected to a lead wire 15 through a conductive adhesive agent 13c. The lead wires 14 and 15 extend through an inside of the circuit substrate 41 to be connected to the oscillation circuit 20.

The material and characteristic of the quartz resonator plate 10 are the same as for those of the first embodiment. The circuit substrate 41 is made of an insulating material provided with a resistance against the sulfuric acid, such as glass, ceramics and plastic etc. and having a coefficient of linear expansion as close to that of the quartz resonator plate 10 as possible and the same as that of the holder tube 11. This is because of a consideration that the coefficient of linear expansion has an influence upon the characteristic frequency of the quartz resonator plate 10 through the deformation.

Figure 11:
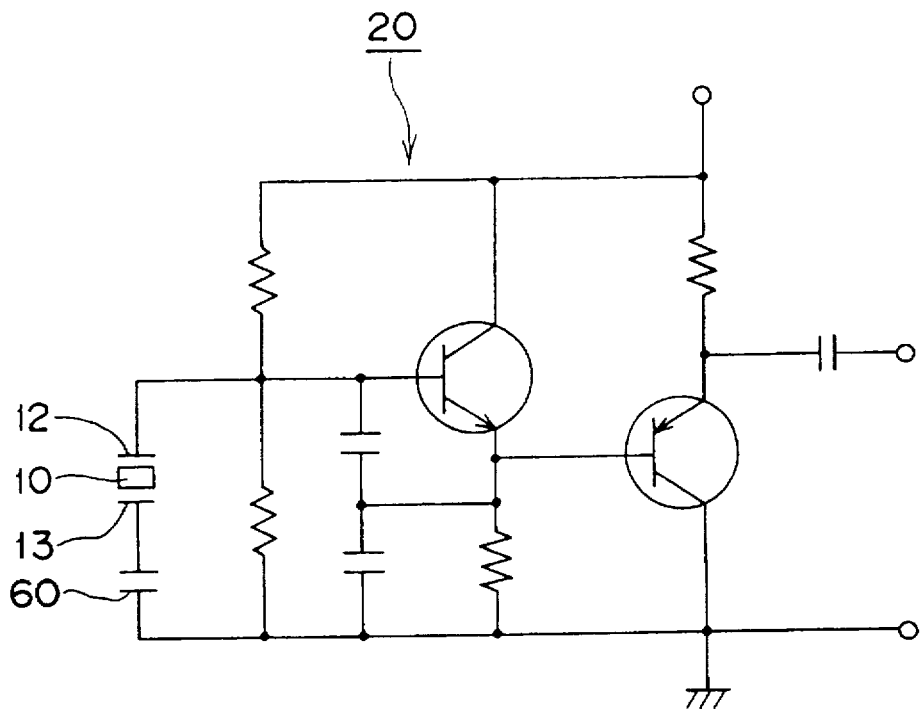
FIG. 11 is a circuit diagram showing an oscillation circuit of embodiment 2.

FIG. 11 is a circuit diagram showing the oscillation circuit 20 for use in this embodiment. This circuit 20 is composed of two transistors. In this circuit 20, the electrode 13 is in a grounded condition through a large capacity condenser 60 in respect of alternative current. For this reason, the oscillation circuit 20 has a characteristic that it can be active to oscillate even if the electrode 13 is changed to be put under a voluntary direct current potential. Accordingly, even in this embodiment, the oscillation circuit 20 is adapted to be supplied power directly from the lead storage battery.

Figure 12:
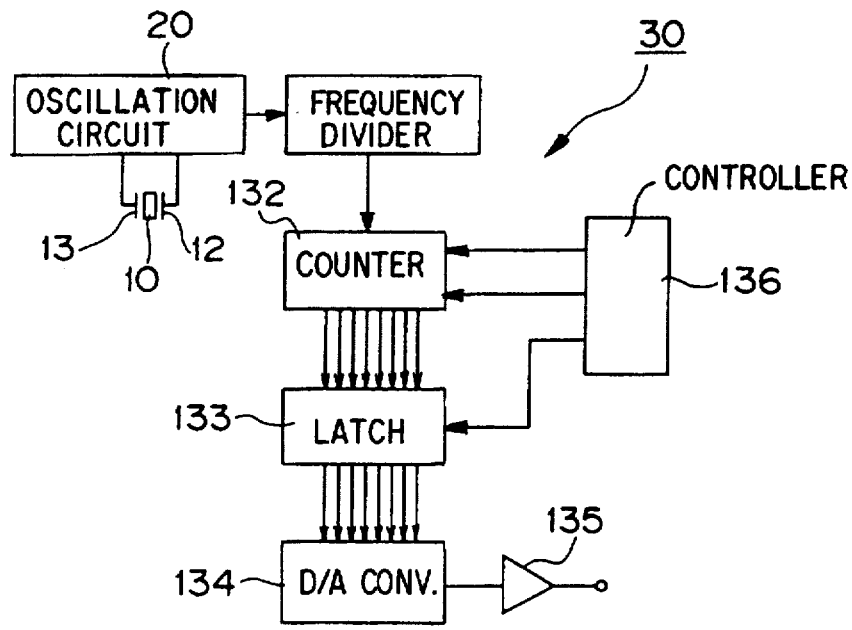
FIG. 12 is a circuit diagram showing an interface circuit of embodiment 2.

FIG. 12 is a circuit diagram showing the interface circuit 30 for use in this embodiment. The interface circuit 30 is adapted to divide an output frequency of the oscillation circuit 20 into a unit of division by passing it through a frequency divider 131, to feed an output to a counter 132, to temporarily store an output in a latch 133, to feed an output to a digital/analogue converter 134, and to amplify an output by a buffer amplifier 135 so as to provide an output signal. The counter 132 operates on receipt of a start pulse and a stop pulse from a gate time controller 136, and the latch 133 also operates on receipt of a latch pulse from the gate time controller 136 in the same way. The frequency output from the oscillation circuit 20 varies depending upon a concentration of an electrolyte which is a subject of the measurement, however, an analogue signal proportional to the above-mentioned frequency change can be output from the buffer amplifier 135 by selecting a dividing ratio of the frequency divider 131 and an effective number of bits of the counter 132, the latch 133 and the digital/analogue converter 134. Further detailed function of the interface circuit 30 will be described as follows. On receipt of the start pulse from the gate time controller 136, the counter 132 commences counting an output frequency of the frequency divider 131. If the effective number of bits of the counter 132 is assumed to be sufficiently large for consideration of this description, the counter 132 does not overflow until the stop pulse is reached after a gate time (one second, for example) has elapsed. After the counting operation is stopped by the stop pulse, bits corresponding to the above-mentioned frequency change amount are stored in the latch 133 by a number of bits of the required resolution and sent to the digital/ analogue converter 134. In this instance, since higher ordered bits above the uppermost bit to be sent to the latch 133 play no role, the effective number of bit of the counter 132 assumed to be sufficiently large may be practically reduced by an amount of meaning nothing. By doing so, the counter 132 will let the unnecessary upper bits overflow during the gate time. Further, since bits at places lower than the lowermost bit to be sent to the latch 133 play no role for the same reason, the effective number of bits of the counter 132 may be reduced by that amount and a dividing ratio of the frequency divider 131 may be increased instead of it. Moreover, the gate time may be shortened instead of using the frequency divider 131. However, since the frequency divider 131 has a function to prolong the gate time to average a dispersion of counted value, a dividing ratio is useful to some extent. Thereby, only the smallest required number of bits can be converted into the analogue signal by the digital/analogue converter 134.

It is also possible to allow an indication using bar-graph by means of code conversion with the digital signals as they are, instead of using the digital/analogue converter 134.

Even in the sulfuric acid concentration sensor of this embodiment, the sulfuric acid concentration can be measured in the same operation as the first embodiment. In this instance, even in this embodiment, the amount of change in the characteristic frequency of the quartz resonator is affected by the changes in the specific gravity and the coefficient of viscosity of the sulfuric acid 6 based on the temperature change. Even in this embodiment, however, since the quartz resonator plate 10 i.e. the quartz resonator itself, is positively provided with the temperature coefficient which offsets the influence based on the above temperature change, an error based on the temperature change in measurement of the sulfuric acid concentration is minimized.

In the sulfuric acid concentration sensor of this embodiment, the electrode 13 at the side contacting the sulfuric acid 6 of the quartz resonator plate 10 is grounded with respect to the alternating current, however, it can operate at a voluntary potential with respect to direct current. The oscillation circuit 20 is active to oscillate normally so that the sulfuric acid concentration can be measured desirably in the lead storage battery, even when it is used for any electrolyte in each chamber with different direct current potential.

Since the holder tube 11 is made of a material having a coefficient of linear expansion as close to that of the quartz resonator plate 10 as possible, there is no chance for the coefficient of linear expansion to influence the characteristic frequency of the quartz resonator plate 10 through the deformation. From this point again, the sulfuric acid concentration can be measured correctly.

When the lead dioxide forming the positive active material softens and falls off so as to adhere to the quartz resonator due to stirring of the electrolyte during charging and discharging of the lead storage battery, the characteristic frequency of the quartz resonator changes to produce a large error in the continual measurements of sulfuric acid concentration up to a termination of the service life of the lead storage battery. In the sulfuric acid concentration sensor of this embodiment, however, there is no chance for the falling-off lead dioxide to adhere to the quartz resonator because the lead dioxide layer is previously formed on the electrode 13 side surface of the quartz resonator plate 10 so as to cover the electrode 13 as well. Therefore, the measurement error caused by the falling-off of lead dioxide forming the positive active material is not produced. Incidentally, fine particles of the lead dioxide are apt to electrostatically adhere to metal, crystal and acrylic resin etc., but lead dioxides do not adhere to each other because of their weak binding forces. Consequently, when the lead dioxide is previously plated onto the quartz resonator, the lead dioxide which falls off does not adhere thereto.

Further, even in the sulfuric acid concentration sensor of this embodiment, the upper end of the quartz resonator plate 10 is positioned at the liquid surface lower limit line 6b of the sulfuric acid 6, so that the sensor also functions as a level gauge in the same way as the first embodiment.

Moreover, the oscillation circuit 20 and the interface circuit 30 are incorporated in the holder tube 11 and thereby located at positions nearer to the place where the measurement is done, than that of the first embodiment so that an influence of electric noise arising within these spaces becomes small as compared with that of the first embodiment. In addition, since the measured values are transmitted by the interface circuit 30 in the form of signal resistant to the electric noise, an influence of electric noise arising between the place and the data processor located at the center of the automobile is also small.

Furthermore, since the quartz resonator plate 10 is installed in the perpendicular position so as to cause bubbles in the sulfuric acid 6 to move and leave a surface of the quartz resonator plate 10, that is, the bubbles are prevented from adhering to the quartz resonator plate 10, so that the function of the quartz resonator plate 10 is securely prevented from being obstructed by the adhesion of bubbles.

Another embodiment

Figure 13:
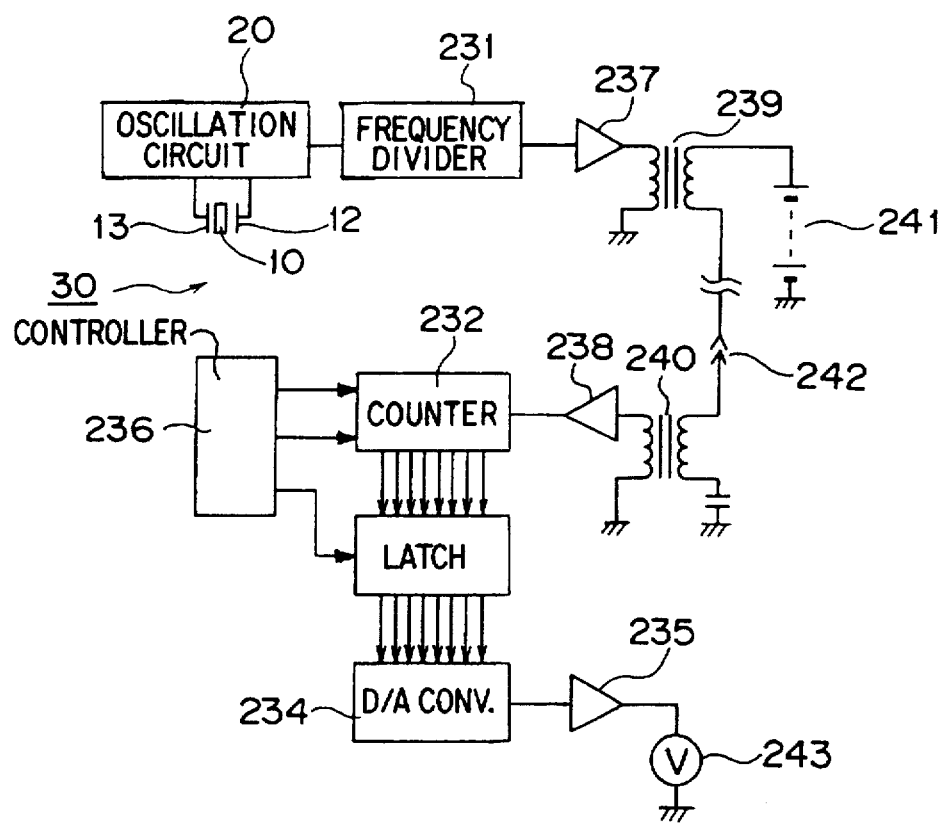
FIG. 13 is a circuit diagram showing an interface circuit of another example.

In embodiments 1 and 2, a circuit having a composition as shown in FIG. 13 may be used for the interface circuit 30. In this interface circuit 30, a high-frequency output signal of a frequency dividing circuit 231 is not directly input to a counter 232 directly, but the signal is amplified by a buffer amplifier 237 and then coupled to a wiring arranged from a lead storage battery 241 which is a subject of measurement, to a cigarette lighter receptacle 242 on a dashboard. A high-frequency signal is picked up from the cigarette lighter receptacle 242 by a high-frequency transformer 240 and amplified by a buffer amplifier 238 so as to be input in the counter 232. The operating principle is the same as that of the circuit shown in FIG. 12, except a point that a signal path is somewhat complicated. However, this interface circuit 30 is adapted to enable an operator to visually confirm a final analogue output signal through means of a voltmeter 243 coupled to the cigarette lighter receptacle 242. When a toroidal core is used for magnetic cores of the high-frequency transformers 239 and 240, and the signal is coupled to an existing wiring of the cigarette lighter having an ordinary low impedance, the only necessary procedure is to let this wiring go through a transmission side toroidal core when installing the circuit, and thereby an advantage is obtainable such that the installation does not require much trouble. The power for a receiver side circuit including the counter 232 may be supplied from the cigarette lighter receptacle 242 through a high-frequency blocking filter.

Figure 14:
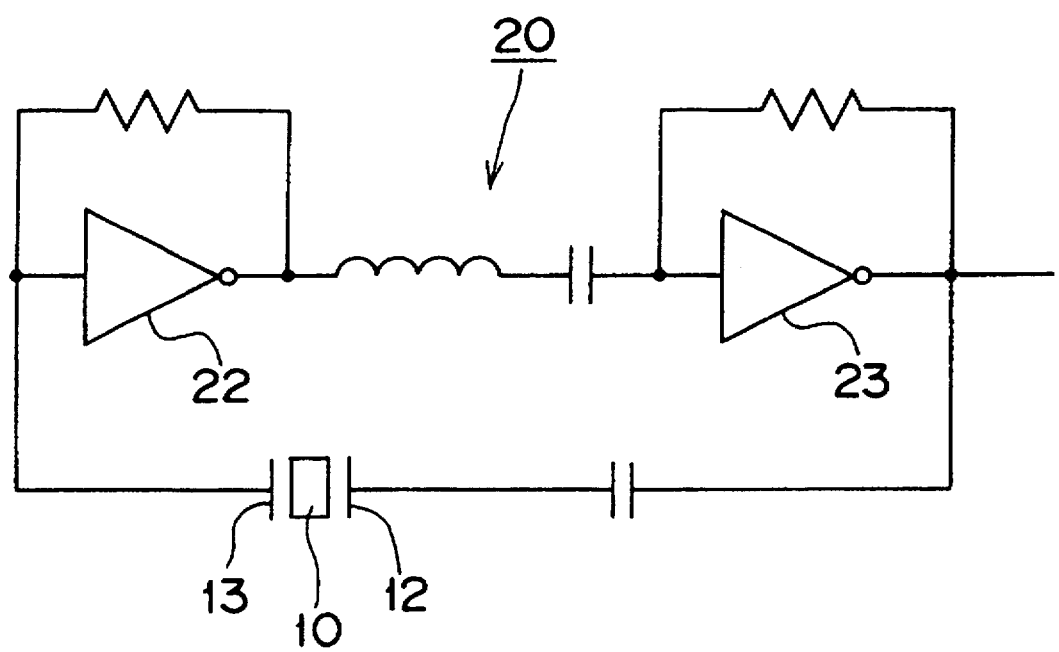
FIG. 14 is a circuit diagram showing an oscillation circuit of another example.

A circuit having a composition shown in FIG. 14 may be used for the oscillation circuit 20. References 22 and 23 denote inverters.

The quartz resonator plate 10 is installed in the horizontal position in embodiment 1, and in the perpendicular position in embodiment 2. But, quartz resonator plate 10 may be installed in an inclined position by changing a shape of a lower end portion of the holder tube 11.

The lead wires 14 and 15 may be formed by being printed with a conductive ink on an inside surface of the holder tube 11 and an inside surface of the circuit substrate 41, by being deposited with a vacuum evaporation method and sputtering method etc., or by sticking a conductive foil using an adhesive agent. By doing so, productivity and vibration resistance can be improved.

A film surface of the electrode 13 in contact with the sulfuric acid 6 may be coated with silicon dioxide or silicon nitride so as to provide it with corrosion resistance.

As described above, according to the sulfuric acid concentration sensors of this invention, the concentration of the sulfuric acid 6 can be determined by obtaining the characteristic frequency of the quartz resonator oscillated in the sulfuric acid 6 forming the electrolyte of the lead storage battery. As a result, the charged condition or residual capacity of the lead storage battery can be detected. For example, if the charging current or charging voltage is decreased when a specific gravity exceeds the specified value of 1.280, an excessive corrosion of the grid can be prevented, water decomposition can be controlled to a minimum and a service life of lead storage battery can be improved conspicuously.

Since the sulfuric acid concentration sensor of this invention is composed of the quartz resonator immersed in the sulfuric acid 6 and the oscillation circuit 20, the composition is simple. In addition, the quartz resonator can be composed of the small quartz resonator plate 10 and the electrodes 12 and 13 installed at both surfaces thereof. Therefore, the sensor can be made small and installed by utilizing the conventional port plug for example, so that the productivity can be improved and the cost can be reduced. Accordingly, the sensor can be used practically for the lead storage battery for an automobile.

The electrode 13 at the side contacting the sulfuric acid 6 of the quartz resonator plate 10 is grounded with respect to the alternating current, so that it can operate at any direct current potential. Therefore, the oscillation circuit 20 is able to oscillate normally, so that it is able to measure the sulfuric acid concentration of electrolyte in any one of several serial chambers of the lead storage battery, each of which is at different potentials.

The quartz resonator plate 10 is installed in the perpendicular position so that bubbles in the sulfuric acid 6 are prevented from adhering to the quartz resonator plate 10, and the function of the quartz resonator plate 10 is securely prevented from being obstructed by the adhesion of any bubbles.

The quartz resonator is provided with the temperature coefficient, which offsets the temperature coefficient of sulfuric acid, so as to minimize an error based on the temperature change so that the characteristic frequency can be measured correctly and the sulfuric acid concentration can thus be obtained exactly.

The lead dioxide layer is previously formed on the surface of the quartz resonator plate 10 contacting the sulfuric acid 6, so that the lead dioxide can be prevented from contacting the quartz resonator even when the lead dioxide forming the positive active material softens and falls off during charging and discharging of the battery. Consequently, the measurement error caused by the falling-off of the lead dioxide forming the positive active material is prevented.

The quartz resonator plate 10 is positioned at the liquid surface lower limit line 6b of the sulfuric acid 6, so that the lowering of the sulfuric acid 6 down below the lower limit line 6b can be detected by the abnormal value. Therefore, this sensor can also function as a level gauge.

The oscillation circuit 20 and the interface circuit 30 are incorporated in the holder tube 11 or the cover portion 51, so that they can be located in the vicinity of the quartz resonator. Therefore, the influence of electric noise can be minimized within these spaces.

The holder tube 11 and the circuit substrate 41 are made of materials having coefficients of linear expansion as close to that of the quartz resonator plate 10 as possible. Accordingly, the characteristic frequency of the quartz resonator plate 10 is prevented from being affected by the coefficient of linear expansion through the deformation. From this point again, the sulfuric acid concentration can be measured correctly.

Since the power of the oscillation circuit 20 is supplied from the lead storage battery which is the subject of measurement, it is not necessary to separately prepare a power source for the sensor. From this point again, the composition of the sensor can be simplified.

What is claimed is:

1. In a sensor for detecting a sulfuric acid concentration of electrolyte for a lead storage battery, a sulfuric acid concentration sensor for the lead storage battery comprising:

a quartz resonator changing its characteristic frequency in an approximately linear relationship according to a change of sulfuric acid concentration, and an oscillation circuit coupled to and oscillating the quartz resonator, the quartz resonator being immersed in an electrolyte such that a characteristic frequency of the quartz resonator during oscillation is obtained so as to determine the sulfuric acid concentration;

wherein the quartz resonator further comprises:

electrodes installed on both surfaces of the quartz resonator plate respectively, each electrode being electrically coupled to the oscillation circuit, the quartz resonator plate being so installed that only one side surface of the plate contacts an electrolyte, and an electrode at the side contacting with the electrolyte being grounded through a condenser in respect of alternating current.

2. A sulfuric acid concentration sensor for a lead storage battery as set forth in claim 1, in which the quartz resonator plate forming the quartz resonator is installed in an inclined position or a perpendicular position.

3. A sulfuric acid concentration sensor for a lead storage battery as set forth in claim 1, wherein the quartz resonator is formed with a quartz resonator plate, the quartz resonator plate being positioned at a liquid surface lower limit line of the electrolyte to function as a level gauge.

4. A sulfuric acid concentration sensor for a lead storage battery as set forth in claim 1, in which the quartz resonator and the oscillation circuit are installed in a port plug of the lead storage battery, the port plug has a immersion portion to be immersed in the electrolyte, the immersion portion comprises a cylindrical portion having an opening, the quartz resonator is so installed as to close said opening to seal an inside of said cylindrical portion, and the oscillation circuit is installed in a cover portion.

5. A sulfuric acid concentration sensor for a lead storage battery as set forth in claim 1, in which the quartz resonator and the oscillation circuit are installed in a port plug of the lead storage battery, the port plug has a immersion portion to be immersed in the electrolyte, the immersion portion comprises a cylindrical portion having an opening, the quartz resonator and the oscillation circuit are installed on a single substrate, and the single substrate is so installed that the oscillation circuit is located in said cylindrical portion and closes said opening so as to seal an inside of said cylindrical portion.

6. A sulfuric acid concentration sensor for a lead storage battery as set forth in claim 1, in which a power of the oscillation circuit is supplied from a lead storage battery a sulfuric acid concentration of which is to be measured.

7. In a sensor for detecting a sulfuric acid concentration of electrolyte for a lead storage battery, a sulfuric acid concentration sensor for the lead storage battery comprising:

a quartz resonator changing its characteristic frequency in an approximately linear relationship according to a change of sulfuric acid concentration, and an oscillation circuit coupled to and oscillating the quartz resonator, the quartz resonator being immersed in an electrolyte such that a characteristic frequency of the quartz resonator during oscillation is obtained so as to determine the sulfuric acid concentration; and wherein the quartz resonator has a temperature coefficient for compensating a temperature coefficient of sulfuric acid.

8. In a sensor for detecting a sulfuric acid concentration of electrolyte for a lead storage battery, a sulfuric acid concentration sensor for the lead storage battery comprising:

a quartz resonator changing its characteristic frequency in an approximately linear relationship according to a change of sulfuric acid concentration, and an oscillation circuit coupled to and oscillating the quartz resonator, the quartz resonator being immersed in an electrolyte such that a characteristic frequency of the quartz resonator during oscillation is obtained so as to determine the sulfuric acid concentration; and wherein lead dioxide is plated on a surface of the quartz resonator at least on a side contacting the electrolyte.

9. In a sensor for detecting a sulfuric acid concentration of electrolyte for a lead storage battery, a sulfuric acid concentration sensor for the lead storage battery comprising:

a quartz resonator changing its characteristic frequency in an approximately linear relationship according to a change of sulfuric acid concentration, and an oscillation circuit coupled to and oscillating the quartz resonator, the quartz resonator being immersed in an electrolyte such that a characteristic frequency of the quartz resonator during oscillation is obtained so as to determine the sulfuric acid concentration;

wherein the quartz resonator and the oscillation circuit are installed in a port plug of the lead storage battery, the port plug has a immersion portion to be immersed in the electrolyte, the immersion portion comprises a cylindrical portion having an opening, the quartz resonator is so installed as to close said opening to seal an inside of said cylindrical portion, and the oscillation circuit is installed in a cover portion; and wherein the immersion portion is made of a material having a coefficient of linear expansion as close as possible to that of a quartz resonator plate forming the quartz resonator.

10. In a sensor for detecting a sulfuric acid concentration of electrolyte for a lead storage battery, a sulfuric acid concentration sensor for the lead storage battery comprising:

a quartz resonator changing its characteristic frequency in an approximately linear relationship according to a change of sulfuric acid concentration, and an oscillation circuit coupled to and oscillating the quartz resonator, the quartz resonator being immersed in an electrolyte such that a characteristic frequency of the quartz resonator during oscillation is obtained so as to determine the sulfuric acid concentration;

wherein the quartz resonator and the oscillation circuit are installed in a port plug of the lead storage battery, the port plug has a immersion portion to be immersed in the electrolyte, the immersion portion comprises a cylindrical portion having an opening, the quartz resonator and the oscillation circuit are installed on a single substrate, and the single substrate is so installed that the oscillation circuit is located in said cylindrical portion and closes said opening so as to seal an inside of said cylindrical portion; and wherein the substrate is made of a material having a coefficient of linear expansion as close to the quartz resonator plate forming the quartz resonator as possible.

* * * * *